US010071035B2

(12) United States Patent
Potnis et al.

(10) Patent No.: US 10,071,035 B2
(45) Date of Patent: Sep. 11, 2018

(54) USE OF BENZYL ALCOHOL AS A DEFOAMING AGENT

(71) Applicant: Colgate-Palmolive Company, Piscataway, NJ (US)

(72) Inventors: Shashank Potnis, Thane (IN); Shridhara Kamath, Mumbai (IN); Amit Sirdesai, Mumbai (IN); Jigna Lapsia, Mumbai (IN); Rolando Plata, Mumbai (IN); Maya Bhansali, Mumbai (IN)

(73) Assignee: Colgate-Palmolive Company, New York, NY (US)

( * ) Notice: Subject to any disclaimer, the term of this patent is extended or adjusted under 35 U.S.C. 154(b) by 98 days.

(21) Appl. No.: 14/937,791

(22) Filed: Nov. 10, 2015

(65) Prior Publication Data
US 2016/0128918 A1 May 12, 2016

(30) Foreign Application Priority Data
Nov. 11, 2014 (IN) .......................... 3253/DEL/2014

(51) Int. Cl.
*A61K 8/34* (2006.01)
*A61K 8/46* (2006.01)
*A61K 8/81* (2006.01)
*A61Q 11/00* (2006.01)

(52) U.S. Cl.
CPC ................ *A61K 8/34* (2013.01); *A61Q 11/00* (2013.01)

(58) Field of Classification Search
CPC ....................................................... A61K 8/34
USPC ..................................... 424/49, 54, 58, 450
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer | |
| 2,658,072 A | 11/1953 | Kosmin | |
| 3,471,927 A | 10/1969 | Eisenberg | |
| 4,303,543 A | 12/1981 | Mansy | |
| 5,292,526 A | 3/1994 | Gaffar et al. | |
| 5,451,396 A | 9/1995 | Villars | |
| 5,705,476 A | 1/1998 | Hoffarth | |
| 5,929,080 A | 8/1999 | Michael et al. | |
| 6,264,926 B1 | 7/2001 | Farooqi et al. | |
| 6,403,652 B1 | 6/2002 | Brahms et al. | |
| 6,500,409 B1 | 12/2002 | Scherl et al. | |
| 7,083,779 B2 | 8/2006 | Behl et al. | |
| 7,297,327 B2 | 11/2007 | Plich et al. | |
| 8,313,884 B2 | 11/2012 | Nosella et al. | |
| 8,362,095 B2 | 1/2013 | Schwab et al. | |
| 2002/0120014 A1* | 8/2002 | Surburg | A23G 4/06 514/715 |
| 2003/0060486 A1* | 3/2003 | Jacob | A61K 9/006 514/320 |
| 2004/0071769 A1* | 4/2004 | Farng | A61K 9/0014 424/450 |
| 2005/0214230 A1* | 9/2005 | Mehta | A61K 8/43 424/49 |
| 2007/0116652 A1 | 5/2007 | Kamath et al. | |
| 2007/0140990 A1 | 6/2007 | Fetissova et al. | |
| 2009/0035229 A1 | 2/2009 | Eirew | |
| 2009/0087501 A1 | 4/2009 | Cummins | |
| 2013/0052237 A1 | 2/2013 | Eliaz et al. | |
| 2013/0064778 A1 | 3/2013 | Riina et al. | |
| 2013/0064779 A1 | 3/2013 | Yamane et al. | |
| 2013/0224125 A1 | 8/2013 | Kolazi et al. | |
| 2013/0224126 A1 | 8/2013 | Lewus et al. | |
| 2013/0230469 A1 | 9/2013 | Lewus et al. | |
| 2013/0266521 A1 | 10/2013 | Fetissova et al. | |
| 2014/0314690 A1 | 10/2014 | Fisher et al. | |

FOREIGN PATENT DOCUMENTS

| | | |
|---|---|---|
| CN | 102010632 | 4/2011 |
| CN | 103233279 | 8/2013 |
| EP | 0102757 | 3/1984 |
| EP | 0967965 | 1/2000 |
| EP | 1633454 | 3/2006 |
| EP | 2275092 | 1/2011 |
| WO | WO98/04234 | 2/1998 |
| WO | WO2004/105914 | 12/2004 |
| WO | WO2008/005550 | 1/2008 |
| WO | WO2008/036299 | 3/2008 |
| WO | WO2011/068815 | 6/2011 |
| WO | WO2011/152819 | 8/2011 |
| WO | WO2012/064338 | 5/2012 |
| WO | WO2012/064341 | 5/2012 |

(Continued)

OTHER PUBLICATIONS

"Benzyl alcohol", http://en.wikipedia.org/wiki/Benzyl_alcohol, accessed Oct. 20, 2014.
Anonymous, "Attention Egg Producers and Egg Washing Facilities", Quality Assurance International, date unknown.
Anonymous, "Benzyl alcohol", www.bechchem.com, accessed Oct. 20, 2014.
Anonymous, "Defoamer Technologies—Agitan", Münzing.
Anonymous, "Defoaming Agents", Shin-Etsu Chemical Co, Ltd., 2012.
Anonymous, "Flofoam defoamer", SNF Floerger.

(Continued)

*Primary Examiner* — Walter E Webb

(57) ABSTRACT

Use of benzyl alcohol as a defoaming agent and an antimicrobial agent in an oral care composition including a surfactant. Also described is a method of manufacturing an oral care composition including forming an oral care base composition, subsequently combining the oral care base composition with a defoaming agent and at least one surfactant to form the oral care composition; and defoaming the oral care composition. The surfactant is combined with the oral care base composition no later than the defoaming agent. The defoaming agent is benzyl alcohol.

16 Claims, No Drawings

(56) References Cited

FOREIGN PATENT DOCUMENTS

WO    WO2014/088536    6/2014

OTHER PUBLICATIONS

Anonymous, "Reduce foaming and air entrapment during mixing", Mixing Technology Insight #36, Charles Ross & Son Company.
Anonymous, "What is a higher alcohol defoamer", http://www.czkeyuan.com/en/News/721830533.html, accessed Oct. 20, 2014.
Clark, 2004. "Hydrolysing esters", http://www.chemguide.co.uk/organicprops/esters/hydrolysis.html, accessed Oct. 20, 2014.
Clayden et al, 2007. Organic Chemistry, Oxford University Press, Oxford, UK, pp. 1102-1103.
CTFA Cosmetic Ingredient Dictionary, 4th Edition, 1991, pp. 509-514.
Exerowa and Kruglyakov 1997, "Foam and foam films: theory, experiment, Application (Google eBook)", Elsevier, pp. 113-114 as published online as www.books.google.co.uk/books?isbn=0080531806.
Hossain et al, 2013. "Evaluation of Some Marketed Cosmetic Products Available in Bangladesh", IJPI's Journal of Pharmaceutics and Cosmetology, vol. 3, issue 13, pp. 24-28.
Kunz et al, "Sipernat and Aerosil for Defoamers", Evonik Industries AG.
McEntree, 2013. "Q&A 357.2—what are the excipients in toothpaste?", UK Medicines Information.
US Code of Federal Regulations, Title 21, vol. 3, Part 173, Section 173.340, revised Apr. 1, 2013.
Wirthensohn et al, 2010. "Investigation of flavour compounds from sweet, semi-bitter and bitter almond kernels", Options Mediterraneennes, A No. 94, XIV GREMPA Meeting on Pistachios and Almonds, pp. 117-122.

* cited by examiner

USE OF BENZYL ALCOHOL AS A DEFOAMING AGENT

CROSS-REFERENCE TO RELATED APPLICATIONS

This present application claims priority to Indian Application No. 3253/DEL/2014, filed Nov. 11, 2014, the contents of which are hereby incorporated by reference in its entirety.

TECHNICAL FIELD

The present invention generally relates to use of benzyl alcohol as a defoaming and an antimicrobial agent in an oral care composition wherein the oral care composition comprises a surfactant. The invention also related to methods for defoaming oral care compositions.

BACKGROUND

The presence of one or more surfactants in a formulation may result in the formation of foam when the formulation is mixed. The formation of foam is often undesirable during manufacturing processes. This is because the foam impacts negatively on mixing processes, potentially degrading the quality of the finished product. Foams are often difficult to handle and it is generally necessary to defoam a product before it can be packed. In addition, foam increases the volume of the product meaning that large void spaces must be left in mixing vessels. Thus it can be seen that the presence of foam reduces the efficiency and reliability of manufacturing processes.

Various methods for preventing the formation of foam have been described. These include the use of chemical defoamers and the selection of mixing conditions to reduce foaming.

A list of defoaming agents suitable for use in food products is provided by the US Code of Federal Regulations Title 21, Volume 3, Part 173, Section 173.340, revised 1 Apr. 2013 (21CFR 173.340) (http://web.archive.org/web/20130914001229/http://www.accessdata.fda.gov/scripts/cdrh/cfdocs/ctcfr/CFRSearch.cfm?FR=173.340).

EP0967965 discloses a low foaming therapeutic toothpaste containing a therapeutic substance, an abrasive, a humectant, a low foam surfactant and/or a foam control agent. Ethanol and low molecular weight polydimethylsiloxanes are identified as foam control agents. Although ethanol is effective as a defoaming agent, its storage, transportation and use are heavily regulated in many jurisdictions. These regulatory requirements make the use of ethanol expensive. The low flash point of ethanol also presents safety and handling concerns. Moreover, ethanol is not acceptable to some consumers for religious reasons. It is therefore desirable to avoid the use of ethanol. Polydimethylsiloxanes are also effective as defoaming agents but are expensive. Furthermore, many silicone oils are not orally acceptable.

There remains a need in the art for improved methods for defoaming oral care compositions.

BRIEF SUMMARY

In one aspect, the present invention provides the use of benzyl alcohol to defoam a composition comprising at least one surfactant, wherein the composition is an oral care composition, and wherein the benzyl alcohol is also used as an antimicrobial agent.

Compositions comprising surfactants may produce foam, for example when mixed or otherwise agitated. It has surprisingly been found that benzyl alcohol acts as a defoaming agent. The presence of benzyl alcohol in a composition reduces the volume of foam generated. Benzyl alcohol accelerates the breakdown of foam relative to a comparative composition which does not include the benzyl alcohol.

The composition is an oral care composition. Benzyl alcohol is particularly useful in oral care compositions because it acts as an antimicrobial agent (see e.g. US2013/0064779) and has an almond-like aroma (Wirthensohn et al, Options Méditerranéennes, 2010, pp 117-122).

Oral care compositions may comprise one or more ingredients selected from abrasives, oral care actives such as anti-caries agents and anti-calculus agents; nutrients such as vitamins; polymers; enzymes; humectants; thickeners; viscosity modifiers; antimicrobial agents; chelating agents; pH adjusting agents; preservatives; flavorings; sweeteners; whitening agents, colorants, herbal extracts and combinations thereof. The oral care composition may be in any conventional form, such as a toothpaste, a tooth gel, or a mouthwash. The oral care composition is preferably a toothpaste. The inclusion of benzyl alcohol in an oral care composition may allow the oral care composition to be substantially free of further preservatives. In particular, it is desirable to formulate oral care compositions which are substantially free of parabens.

The oral care composition may include a copolymer of methyl vinyl ether and maleic anhydride. The oral care composition may include a halogenated diphenyl ether, e.g. triclosan.

The composition comprises at least one surfactant. The nature of the at least one surfactant is not particularly limited. The at least one surfactant may comprise an anionic surfactant. One example of an anionic surfactant is sodium lauryl sulfate. Sodium lauryl sulfate is inexpensive and is available in both liquid and solid forms, meaning that it is compatible with a broad variety of manufacturing processes. A further example of an anionic surfactant is sodium lauroyl sarcosinate.

The at least one surfactant may comprise a non-ionic surfactant. The non-ionic surfactant may be a polysorbate, for example polysorbate 20 or polysorbate 80. Polysorbates are available from ICI Americas, Inc under the trade name "TWEEN".

Other examples of surfactants include betaine surfactants and poloxamer surfactants. Mixtures of surfactants may be used. One example of a mixture comprises sodium lauryl sulfate, a betaine and a poloxamer.

The amount of surfactant present in the composition may be, for example, up to 5% by weight of the composition. The surfactant may be present in an amount of 0.5% to 5% by weight of the composition and preferably 1.5% to 3% weight of the composition.

Benzyl alcohol may be used in an amount in the range 0.1% to 0.7% by weight of the composition, or preferably in an amount in the range 0.25% to 0.35% by weight of the composition. Amounts in these ranges were found to be effective in reducing the amount of foaming during the manufacture of a composition, without rendering the finished composition incapable of foaming. These ranges are particularly well adapted for toothpaste compositions. Toothpaste compositions must have a minimum foaming power to satisfy regulatory requirements in certain nations, e.g. in India.

Benzyl alcohol may be used in combination with a foam-reducing flavour. It has surprisingly been found that a stronger defoaming effect is obtained when benzyl alcohol is used in combination with a foam-reducing flavour. A foam-reducing flavour is a flavour which reduces the surface energy of air bubbles in water. Useful foam-reducing flavours include oils and alcohols. Oils may form a thin layer having a lower surface tension than water. Alcohols may reduce the surface tension and density of water. The foam-reducing flavour may comprise one or more essential oils, e.g. oils extracted from a plant by distillation. The foam-reducing flavour may be selected from: vanillin; sage; marjoram; parsley oil; spearmint oil; cinnamon oil; oil of wintergreen (methyl salicylate); peppermint oil; clove oil; bay oil; anise oil; *eucalyptus* oil; citrus oils; fruit oils and essences including those derived from lemon, orange, lime, grapefruit, apricot, banana, grape, apple, strawberry, cherry, pineapple; etc. bean- and nut-derived flavours such as coffee, cocoa, cola, peanut, almond, etc.; and menthol, menthyl acetate, menthyl lactate, camphor, *eucalyptus* oil, eucalyptol, anethole, eugenol, *cassia*, oxanone, a-irisone, propenyl guaiethol, thymol, linalool, benzaldehyde, cinnamaldehyde, N,2,3-trimethyl-2-isopropylbutanamide, 3-(1-menthoxy)-propane-1,2-diol, cinnamaldehyde glycerol acetal (CGA), and menthone glycerol acetal (MGA). Preferred foam-reducing flavours include those having 8 to 12 carbon atoms, at least one terminal dimethyl group, and a non-terminal OH group. The use of a foam reducing flavour is preferred, but also contemplated herein is the use of other oils or alcohols.

The foam-reducing flavour may be used in an amount in the range 0.1% to 5% by weight of the composition. The foam-reducing flavour may preferably be used in an amount in the range 0.5% to 1.5% by weight of the composition. An alternative preferred range is 4.5% to 5% by weight of the composition.

The use may include forming a pre-mix comprising the benzyl alcohol and the at least one surfactant, and combining the pre-mix with the composition. In the arrangements where a foam-reducing flavour is used, the pre-mix may further comprise the foam-reducing flavour. The pre-mix may comprise one or more further ingredients. The further ingredients are suitably more soluble in the pre-mix than in the composition.

The use may be in a method of manufacturing an oral care composition, which method comprises: (a) forming an oral care base composition; (b) subsequently combining the oral care base composition with a defoaming agent and at least one surfactant to form the oral care composition; and (c) defoaming the oral care composition, wherein the defoaming agent is benzyl alcohol; and wherein the defoaming agent is combined with the oral care base composition no later than the at least one surfactant. By combining the benzyl alcohol with the oral care base no later than the surfactant, the initial formation of foam is inhibited or prevented. This allows for the more rapid manufacture of the oral care composition.

Particularly preferably, step (b) comprises combining a pre-mix with the oral care base composition. The pre-mix comprises the defoaming agent the at least one surfactant. Most preferably, the pre-mix further comprises a foam-reducing flavour.

Alternatively or additionally, the use may be in a method of manufacturing an oral care composition which method comprises the steps of: (i) mixing benzyl alcohol and at least one surfactant with an oral care base composition; and (ii) stirring the resulting mixture under vacuum to defoam the mixture; wherein the vacuum is applied no later than 4 minutes after step (i). In conventional methods, the composition is stirred for an extended period e.g. 5 minutes or more after adding the surfactant before applying the vacuum. In methods which make use of benzyl alcohol, the stir time may be reduced. Reduced stir times allow the faster manufacture of the oral care composition.

In another aspect, the present invention provides a method of manufacturing an oral care composition, which method comprises:
 (a) forming an oral care base composition;
 (b) subsequently combining the oral care base composition with a defoaming agent and at least one surfactant to form the oral care composition; and
 (c) defoaming the oral care composition,
wherein the defaming agent is benzyl alcohol; and
wherein the defoaming agent is combined with the oral care base composition no later than the at least one surfactant. This method makes use of benzyl alcohol as a defoaming agent. The defoaming effect of benzyl alcohol may allow the length of the defoaming step to be reduced. The defoaming effect may allow a larger batch to be produced in a given vessel. In this way, the use of benzyl alcohol in the methods described herein improves the efficiency of the manufacturing process.

Benzyl alcohol may be included in the oral care composition in an amount in the range 0.1% to 0.7% by weight of the oral care composition, or in an amount in the range 0.25% to 0.35% by weight of the oral care composition. Amounts in these ranges were found to be effective in reducing the amount of foam generated during the method of manufacture while allowing the composition to generate some foam, as is required by certain regulatory standards.

Benzyl alcohol also acts as an antimicrobial agent. The foam-reducing flavour, if present, may also provide antimicrobial activity. Hence, the oral care composition may be substantially free of further preservatives. Preferably, the oral care composition is substantially free of parabens. In this context, "substantially free" means that trace amounts of further preservatives may be present but that these amounts would be insufficient to provide a preservative effect. For example, a composition which is substantially free of further preservatives may comprise further preservatives or parabens in an amount of up to 10 ppm by weight of the composition.

One or more further preservatives may however be included in the composition if desired. The one or more further preservatives may be present in an amount in the range 0% to 5% by weight of the composition.

The nature of the at least one surfactant is not particularly limited. Suitably, the surfactant will be suitable for use in an oral care composition. The surfactant may comprise an anionic surfactant. The anionic surfactant may be sodium lauryl sulfate. Sodium lauryl sulfate is available in the form of a solid or a liquid. It is convenient to be able to select the physical form of the surfactant depending on the nature of the manufacturing process. Sodium lauryl sulfate is widely available commercially and is inexpensive. A further example of an anionic surfactant is sodium lauroyl sarcosinate.

The surfactant may comprise a betaine surfactant, a polysorbate surfactant, and/or a poloxamer surfactant. Other surfactants may be used.

Combinations of two or more surfactants may be used. A preferred combination comprises sodium lauryl sulfate, a betaine surfactant and a poloxamer surfactant.

The amount of surfactant present in the composition is not particularly limited and may be selected depending on the nature of the surfactant and the desired properties of the composition. The surfactant may, for example, be present in an amount of up to 5% by weight of the composition. The surfactant may be present in an amount of 0.5% to 5% by weight of the composition, or 1.5% to 3% by weight of the composition.

The oral care composition may comprise a foam-reducing flavour. Surprisingly, foam-reducing flavours produce a synergistic effect when used in combination with benzyl alcohol. A foam-reducing flavour is a flavour which reduces the surface energy of air bubbles in water. Useful foam-reducing flavours include oils and alcohols. Oils may form a thin layer having a lower surface tension than water. Alcohols may reduce the surface tension and density of water. The foam-reducing flavour may comprise one or more essential oils, e.g. oils extracted from a plant by distillation. The foam-reducing flavour may be selected from: vanillin; sage; marjoram; parsley oil; spearmint oil; cinnamon oil; oil of wintergreen (methyl salicylate); peppermint oil; clove oil; bay oil; anise oil; *eucalyptus* oil; citrus oils; fruit oils and essences including those derived from lemon, orange, lime, grapefruit, apricot, banana, grape, apple, strawberry, cherry, pineapple; etc. bean- and nut-derived flavours such as coffee, cocoa, cola, peanut, almond, etc.; and menthol, menthyl acetate, menthyl lactate, camphor, *eucalyptus* oil, eucalyptol, anethole, eugenol, *cassia*, oxanone, a-irisone, propenyl guaiethol, thymol, linalool, benzaldehyde, cinnamaldehyde, N,2,3-trimethyl-2-isopropylbutanamide, 3-(1-menthoxy)-propane-1,2-diol, cinnamaldehyde glycerol acetal (CGA), and menthone glycerol acetal (MGA). Preferred foam-reducing flavours include those having 8 to 12 carbon atoms, at least one terminal dimethyl group, and a non-terminal OH group. The use of a foam reducing flavour is preferred, but also contemplated herein is the use of other oils or alcohols.

The foam-reducing flavour may be included in the oral care composition in an amount in the range 0.1% to 5% by weight of the composition. The foam-reducing flavour may preferably be used in an amount in the range 0.5% to 1.5% by weight of the composition. An alternative preferred range is 4.5% to 5% by weight of the composition.

In the arrangements where the oral care composition is to include a foam-reducing flavour, step (b) of the method may comprise:
(i) forming a pre-mix comprising the defoaming agent and the foam-reducing flavour; and
(ii) combining the pre-mix with the oral care base composition.

Forming a pre-mix in this way means that the benzyl alcohol and the foam-reducing flavour are introduced into the oral care composition at the same time. Foam-reducing flavours may be poorly soluble in certain oral care compositions. Forming a pre-mix comprising the foam-reducing flavour and the benzyl alcohol may help to solubilize the foam-reducing flavour. Pre-mixes are also believed to provide a stronger defoaming effect in comparison to the separate addition of foam-reducing flavour and benzyl alcohol.

The pre-mix may comprise the surfactant. Including the surfactant in the pre-mix prevents the formation of foam. High concentrations of benzyl alcohol provide a strong defoaming effect. Without wishing to be bound by theory, it is believed that when a pre-mix is used, the surfactant is exposed to a higher effective local concentration of benzyl alcohol as it is mixed with the oral care base composition.

The pre-mix may further comprise a lipophilic ingredient. As used herein, the term "lipophilic ingredient" refers in particular to those materials which have a greater solubility in benzyl alcohol and/or the foam-reducing flavour than in water. Dissolving lipophilic ingredients in the pre-mix allows the lipophilic ingredient to mix with the oral care composition more easily, thereby improving the uniformity of the composition and reducing the amount of stirring needed.

The lipophilic ingredient may be an oral care active, such as a halogenated diphenyl ether. The halogenated diphenyl ether may be triclosan. The halogenated diphenyl ether may be included in the composition in an amount in the range 0.2% to 0.4% by weight of the composition. Other examples of lipophilic ingredients include herbal extracts.

The oral care base composition may be formed by any suitable method. For example, step (a) of the method may comprise:
(i) forming a gel comprising a humectant; and
(ii) combining the gel with one or more further components to form the oral care base composition;
wherein the further components comprise one or more of a thickener and an abrasive. The manufacture of may oral care compositions involves the formation of a gel phase.

Various methods may be used to defoam the composition. For example, step (c) may comprise stirring the oral care composition under vacuum. Oral care compositions, particularly toothpastes, often have a thick consistency. Stirring at a pressure which is below atmospheric pressure therefore helps to remove entrapped air from the composition. For example, a pressure of 66 kPa to 93 kPa (500 mm Hg to 700 mm Hg) may be used, and preferably a pressure of 80 kPa to 93 kPa (about 600 mm Hg to about 700 mm Hg). These pressure ranges are particularly well adapted for defoaming toothpaste compositions. A weaker vacuum, e.g. pressures in the range from 94 kPa to 100 kPa, may be appropriate for other forms of compositions such as emulsions and creams.

The use of a vacuum is optional. Step (c) may comprise allowing the composition to settle at room temperature and pressure. For compositions which are in the form of syrups or suspensions, it is preferable to allow the composition to settle at ambient pressure without applying a vacuum. Step (c) may have a duration of 12 minutes or less, or 10 minutes or less, or most preferably 5 minutes or less.

In another aspect, the present invention provides a method of using benzyl alcohol as a defoaming agent in the manufacture of an oral care composition, which method comprises the steps of:
(i) mixing benzyl alcohol and a surfactant with an oral care base composition; and
(ii) stirring the resulting mixture under vacuum to defoam the mixture;
wherein the vacuum is applied within about 4 minutes of step (i).

This method makes use of the surprising ability of benzyl alcohol to act as a defoaming agent. In this method, the benzyl alcohol and the surfactant are mixed with the oral care base composition at about the same time, and vacuum is applied. This is in contrast to conventional processes, in which an extended stir time is used between the addition of the surfactant and the application of the vacuum. By using benzyl alcohol foaming is prevented and the stir time before vacuum is applied may be reduced.

Step (i) may comprise mixing a foam-reducing flavour with the oral care base composition. It has been found that the defoaming effect is stronger when benzyl alcohol is used in combination with a foam-reducing flavour. A foam-reducing flavour is a flavour which reduces the surface energy of air bubbles in water. Useful foam-reducing flavours include oils and alcohols. Oils may form a thin layer having a lower surface tension than water. Alcohols may reduce the surface tension and density of water. The foam-reducing flavour may comprise one or more essential oils, e.g. oils extracted from a plant by distillation. The foam-reducing flavour may be selected from: vanillin; sage; marjoram; parsley oil; spearmint oil; cinnamon oil; oil of wintergreen (methyl salicylate); peppermint oil; clove oil; bay oil; anise oil; *eucalyptus* oil; citrus oils; fruit oils and essences including those derived from lemon, orange, lime, grapefruit, apricot, banana, grape, apple, strawberry, cherry, pineapple; etc. bean- and nut-derived flavours such as coffee, cocoa, cola, peanut, almond, etc.; and menthol, menthyl acetate, menthyl lactate, camphor, *eucalyptus* oil, eucalyptol, anethole, eugenol, *cassia*, oxanone, a-irisone, propenyl guaiethol, thymol, linalool, benzaldehyde, cinnamaldehyde, N,2,3-trimethyl-2-isopropylbutanamide, 3-(1-menthoxy)-propane-1,2-diol, cinnamaldehyde glycerol acetal (CGA), and menthone glycerol acetal (MGA). Preferred foam-reducing flavours include those having 8 to 12 carbon atoms, at least one terminal dimethyl group, and a non-terminal OH group. The use of a foam reducing flavour is preferred, but also contemplated herein is the use of other oils or alcohols.

The method may comprise the step of forming a pre-mix before step (i). The pre-mix may comprise the benzyl alcohol and the surfactant. The pre-mix may comprise the benzyl alcohol and the foam-reducing flavour. The pre-mix may comprise the benzyl alcohol, the foam-reducing flavour, and the surfactant. As described above, forming a pre-mix may help to solubilize the foam-reducing flavour and/or to enhance the defoaming activity of the benzyl alcohol.

The benzyl alcohol may be included in the oral care composition in an amount in the range 0.1% to 0.7%, and preferably in an amount in the range 0.25% to 0.35% by weight of the oral care composition. These ranges provide a defoaming effect during manufacture while permitting the oral care composition to have adequate foaming power.

The surfactant may comprise an anionic surfactant. Examples of preferred anionic surfactants include sodium lauryl sulfate and sodium lauroyl sarcosinate. The surfactant may comprise a betaine surfactant and/or a poloxamer surfactant. Mixtures of surfactants may be used.

The vacuum is applied within about 4 minutes of step (i). The vacuum may be applied within about 3 minutes of step (i). More preferably, the vacuum may be applied within about 2 minutes of step (i). In a conventional process, vacuum is not applied until 5 minutes or more have passed after the addition of the surfactant. This is because large amounts of foam would be generated if the vacuum is applied before the surfactant is distributed throughout the composition. It has been found that when benzyl alcohol is used as a defoaming step, it is not necessary to stir the composition for an extended period of time between adding the surfactant and applying the vacuum. The use of benzyl alcohol therefore allows for the faster manufacture of the oral care composition.

As used herein, stirring under vacuum means stirring the composition under a pressure which is less than atmospheric pressure (about 101 kPa (760 mm Hg) at sea level). For example, a pressure of 66 kPa to 93 kPa (500 mm Hg to 700 mm Hg) may be used, and preferably a pressure of 80 kPa to 93 kPa (about 600 mm Hg to about 700 mm Hg).

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

It has surprisingly been found that benzyl alcohol is useful for defoaming compositions comprising at least one surfactant.

Benzyl alcohol is an aromatic alcohol which is also known under the names phenylmethanol and phenylcarbinol. At room temperature and pressure, benzyl alcohol is an oily liquid. Benzyl alcohol has an aqueous solubility of 4.29 g/mL at 25° C. The boiling point of benzyl alcohol is 205° C. at a pressure of about 1 atm (approximately 101 kPa). This is higher than the boiling points of methanol (64.7° C.) and ethanol (78.4° C.).

Using a defoaming agent with a high boiling point is advantageous because the manufacture of many compositions involves the use of elevated temperatures for at least part of the manufacturing process. For example, in the manufacture of oral care compositions ingredients are often mixed at temperatures in the range 60 to 70° C. Temperatures of up to 80° C. are used for some applications. Temperatures during manufacture may therefore approach or even exceed the boiling point of ethanol. Evaporative losses of ethanol from the composition under such conditions would be significant. The evaporation of ethanol poses a fire hazard and may necessitate the use of a flame proof vessel or manufacturing facility. The high boiling point of benzyl alcohol avoids these risks.

Benzyl alcohol has been reported to be useful as an antimicrobial agent in oral care compositions (US2013/0064779; WO2012/064341). Benzyl alcohol has further been identified as one of the compounds responsible for the flavour and aroma of bitter and semi-bitter almonds (Wirthensohn et al, Options Méditerranéennes, A. no 94, 2010—XIV GREMPA Meeting on Pistachios and Almonds).

As used herein, defoaming encompasses accelerating the breakdown of an existing foam. Preventing or reducing the formation of foam is also encompassed.

"Manufacturing" generally refers to a process which comprises combining one or more ingredients, for example by mixing, to form a composition. The composition is optionally packed into a receptacle after manufacturing.

The composition comprises at least one surfactant. The nature of the composition is otherwise not particularly limited. The use of benzyl alcohol in a broad variety of compositions is contemplated. The composition may suitably be in the form of a liquid, a gel, or a paste. The composition will typically comprise water.

The nature of the at least one surfactant is not particularly limited, and will be selected depending on the nature and intended use of the composition. The at least one surfactant may be selected from anionic, nonionic, cationic, zwitterionic, amphoteric, ampholytic surfactants and combinations thereof.

The at least one surfactant may comprise an anionic surfactant. Examples of anionic surfactants which are particularly useful in oral care compositions include fatty acid monoglyceride monosulfates, higher alkyl sulfates (e.g., sodium lauryl sulfate); higher alkyl aryl sulfonates, (e.g., sodium linear dodecyl benzene sulfonate), higher olefin sulfonates (e.g., sodium higher olefin sulfonate), higher alkyl alkali sulfoacetates (e.g., sodium lauryl sulfoacetate); higher fatty acid esters of 1,2-dihydroxypropane sulfonates; the substantially saturated higher aliphatic acyl amides of lower aliphatic aminocarboxylic acid alkali metal salts, (e.g, having 12 to 16 carbon atoms in the fatty acyl radicals), higher alkyl poly-lower alkoxy (of 10 to 100 alkoxies) sodium sulfates, higher fatty acid sodium and potassium soaps of coconut oil and tallow. The anionic surfactant may be selected from sodium lauryl sulfate, sodium laureth sulfate, sodium lauroyl sarcosinate, and mixtures thereof. The anionic surfactant may be sodium lauryl sulfate.

Examples of suitable water soluble nonionic surfactants include the polymeric condensation products of hydrophilic alkylene oxide group-containing compounds (typically ethylene oxide) with organic hydrophobic compounds (for example those having aliphatic chains of about 12 to 20 carbon atoms). Such products include the "ethoxamers" and include for example the condensation products of poly (ethylene oxide) with fatty acids, fatty alcohols, fatty amides and other fatty moieties, as well as with propylene oxide and polypropylene oxides (the latter being available, for example, under the trade name Pluronic®). Preferred nonionic surfactants include polysorbates, such as polysorbate 20 and polysorbate 80. Polysorbate surfactants are sold under the trade name Tween.

Examples of zwitterionic surfactants include those which may be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. Examples include: 4-[N, N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-P-diethyl-P-3,6, 9trioxatetradecyl-phosphonio]-2-hydroxypropane-1-phosphate; 3-[N,N-dipropyl-N-3dodecoxy-2-hydroxypropylammonio]-propane-1-phosphonate; 3-(N,N-di-methy-N-hexadecylammonio)propane-1-sulfonate; 3-(N, N-dimethyl-N-hexadecylammonio)-2-hydroxypropane-1-sulfonate; 4-(N,N-di(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio) propane-1-phosphonate; and 5-[N,N-di(3-hydroxypropyl)-N-hexadecylammonio]-2-hydroxy-pentane-1-sulfate.

Examples of amphoteric surfactants include those which can be broadly described as derivatives of aliphatic secondary and tertiary amines in which the aliphatic radical can be straight chain or branched and wherein one of the aliphatic substituents contains from 8 to 18 carbon atoms and one contains an anionic water solubilizing group, e.g., carboxy, sulfonate, sulfate, phosphate, or phosphonate. Examples of compounds falling within this definition are sodium 3-dodecylaminopropionate and sodium 3-dodecylaminopropane sulfonate. Further amphoteric surfactants are described in U.S. Pat. No. 2,658,072, U.S. Pat. No. 2,438,091 and U.S. Pat. No. 2,528,378.

The preferred amphoteric surfactants are betaines. Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl) carboxy methyl betaine, stearyl bis-(2-hydroxypropyl)carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned: stearyldimenthylbenzyl ammonium chloride; dodecyltrimethylammonium chloride; nonylbenzylethyldimethyl ammonium nitrate; tetradecylpyridinium bromide; laurylpyridinium chloride; cetylpyridinium chloride; laurylpyridinium chloride; laurylisoquinolium bromide; ditallow (Hydrogenated) dimethyl ammonium chloride; dilauryldimethyl ammonium chloride; and stearalkonium chloride.

Additional cationic surfactants are disclosed in U.S. Pat. No. 4,303,543. Also see CTFA Cosmetic Ingredient Dictionary, 4th Edition 1991, pages 509-514 for various long chain alkyl cationic surfactants.

Preferred surfactants include betaines, polysorbates, poloxamers and anionic surfactants, particularly sodium lauryl sulfate.

The amount of surfactant present in the composition may be selected as appropriate. For example, the surfactant may be present in the composition in an amount of up to 5% by weight of the composition. The surfactant may be present in an amount of 0.5% to 5% by weight of the composition, or 1.5% to 3% by weight of the composition. These ranges of amounts are particularly well-suited to oral care compositions.

The composition is an oral care composition. This allows the use of the flavour, aroma, and antibacterial properties of benzyl alcohol in addition to its defoaming properties. Examples of oral care compositions include toothpastes, tooth gels, and mouthwashes. Toothpastes and tooth gels typically comprise larger concentrations of surfactants than mouthwashes. It is particularly desirable therefore to provide a defoaming agent for toothpastes and tooth gels.

Oral care compositions such as toothpastes and tooth gels may for example comprise one or more ingredients selected from abrasives, oral care actives such as anti-caries agents and anti-calculus agents; nutrients such as vitamins; polymers; enzymes; humectants; thickeners; viscosity modifiers; antimicrobial agents; chelating agents; pH adjusting agents; preservatives; flavorings; sweeteners; whitening agents, colorants, herbal extracts and combinations thereof. It will be appreciated that these categories of ingredients are not necessarily mutually exclusive. For example, some humectants are known to act as sweeteners.

Oral care compositions may comprise a solvent. The solvent generally comprises water. The solvent may alternatively or additionally comprise an organic solvent, such as ethanol. Dual-phase mouthwash compositions comprising an aqueous solvent and an immiscible organic solvent are contemplated herein.

Examples of anti-caries agents include fluoride sources. The fluoride source may be selected from sodium fluoride, potassium fluoride, potassium monofluorophosphate, sodium monofluorophosphate, ammonium monofluorophosphate, sodium fluorosilicate, ammonium fluorosilicate, an amine fluoride, ammonium fluoride, and combinations thereof. One example of an amine fluoride is Olaflur (N'-octadecyltrimethylendiamine-N,N,N'-tris(2-ethanol)-dihydrofluoride). Preferred fluoride sources include sodium fluoride, amine fluorides, sodium monofluorophosphate, and mixtures thereof. A particularly preferred fluoride source is sodium monofluorophosphate.

The fluoride source may be present in an amount sufficient to supply 50 to 5000 ppm fluoride ion, e.g., from 100 to 1000 ppm, from 200 to 500, or 250 ppm fluoride ion. Fluoride ion sources may be added to the compositions in an amount of 0.001% to 10%, e.g., from 0.003% to 5%, 0.01% to 1, or 0.05% by weight of the composition. However, it is to be understood that the weights of fluoride salts to provide the appropriate level of fluoride ion will obviously vary based on the weight of the counter ion in the salt, and that one of skill in the art may readily determine such amounts.

Examples of oral care actives include zinc ions. The oral care compositions may comprise a source of zinc ions. One or more such sources can be present. The zinc ion source(s) may be present in a total amount of from 0.05% to 3%, for example from 0.1% to 1%, by weight of the composition. Suitable zinc ion sources include without limitation zinc oxide, zinc acetate, zinc citrate, zinc gluconate, zinc glycinate, zinc oxide, zinc sulfate, sodium zinc citrate and mixtures thereof.

Basic amino acids, such as arginine, and their salts and derivatives have also been reported to have anti-caries effects and may usefully be included in oral care compositions.

The oral care compositions described herein may comprise an abrasive. The abrasive may be an abrasive silica or calcium carbonate.

Abrasive silicas are distinct from thickening silicas. In general, abrasive (cleaning) silicas can be characterized as having oil absorption levels of about 40 to 150 cc/100 g and having an Einlehner abrasion of 3 or greater mg loss/100,000 revolutions whereas thickening abrasives have oil absorption levels of greater than 150 cc/100 g and having an Einlehner abrasion of less than 2 mg loss/100,000 revolutions. Abrasive silicas include silica abrasives such as precipitated or hydrated silicas having a mean particle size of up to about 20 microns, such as Zeodent 103, 105, 113, 114, 115, or 124 marketed by J.M. Huber Chemicals Division, Havre de Grace, Md. 21078, Sylodent 783 marketed by Davison Chemical Division of W.R. Grace & Company, Sorbosil AC 43 from PQ Corporation, and mixtures thereof.

Other abrasives include aluminium oxide, aluminium silicate, calcined alumina, bentonite or other siliceous materials, insoluble phosphates, calcium carbonate, and mixtures thereof.

An abrasive or mixture of abrasives may be present in an amount of from 5 to 35%, optionally from 10 to 20%, and further optionally from 12 to 17% by weight of the composition.

The composition may comprise a thickener. Thickeners are useful for imparting a desired consistency and/or mouth feel to the composition. Any orally acceptable thickening agent may be used, including carbomers (also known as carboxyvinyl polymers); carrageenans (also known as Irish moss and more particularly i-carrageenan (iota-carrageenan)); cellulosic polymers such as hydroxyethylcellulose, carboxymethylcellulose (CMC) and salts thereof, e.g., CMC sodium; natural gums such as karaya, xanthan, gum arabic and tragacanth; colloidal magnesium aluminum silicate; colloidal silica and the like. Preferred thickeners include a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof.

Silica thickeners such as Zeodent 115 and Zeodent 165 (both available from Huber Engineered Materials) and DT 267 (available from PPG Industries or OSC-Lianji Chemical industry Co., Ltd.) may also be used.

The thickener may be present in a total amount of from 0.01% to 15%, for example from 0.1% to 10%, or from 0.2% to 5% by weight of the composition.

The composition may comprise a viscosity modifier, useful for example for inhibiting settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from 0.01% to 10%, for example, from 0.1% to 5% by weight of the composition.

The composition may comprise a humectant. Any orally acceptable humectant can be used, including without limitation polyhydric alcohols such as glycerine, sorbitol (particularly as a 70% solution), xylitol or low molecular weight polyethylene glycols (PEGs) such as PEG 600. Many humectants also function as sweeteners. One or more humectants are optionally present in an amount of from 1% to 70%, for example, from 1% to 50%, from 2% to 25%, or from 5% to 15% by weight of the composition.

The composition may comprise a sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (such as sodium saccharin), dipeptide-based intense sweeteners, cyclamates and the like. One or more sweeteners are optionally present in a total amount depending strongly on the particular sweetener(s) selected, but typically 0.005% to 5%, optionally 0.005% to 0.3%, further optionally 0.05% to 0.1% by total weight of the composition.

The composition may comprise an antimicrobial agent such as chlorhexidine, a halogenated diphenyl ether (e.g. triclosan), quaternary ammonium compounds (for example benzalkonium chloride) or an additional preservative agent such as a paraben (for example methylparaben or propylparaben). The preferred antimicrobial agent is triclosan. One or more antibacterial or preservative agent is optionally present in the composition in a total amount of from 0.01% to 0.5%, optionally 0.05% to 0.1% by weight of the composition.

The composition may comprise a whitening agent. Suitable whitening agents include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites include calcium chlorite, barium chlorite, magnesium chlorite, lithium chlorite, sodium chlorite, and potassium chlorite. Such agents may be added in effective amounts, e.g., from 1% to 20% by weight of the composition, depending on the agent chosen.

Oral care compositions may comprise an anti-calculus agent, such as, for example, one or more of the anti-calculus compositions discussed in U.S. Pat. No. 5,292,526 to Gaffar et al. The anti-calculus composition may include one or more polyphosphates. The anti-calculus composition may include at least one wholly or partially neutralized alkali metal or ammonium tripolyphosphate or hexametaphosphate salt present in the oral composition at an effective anti-calculus amount. The anti-calculus active may also include at least one water soluble, linear, molecularly dehydrated polyphosphate salt in an effective anti-calculus amount. The anti-calculus active may also include a mixture of potassium and sodium salts, at least one of which is present in an effective anti-calculus amount as a polyphosphate anti-calculus agent. The anti-calculus active agent may also contain an effective anti-calculus amount of linear molecularly dehydrated polyphosphate salt anti-calculus agent present in a mixture of sodium and potassium salts. The ratio of potassium to sodium in the composition can be 3:1 or less. The polyphosphate may be present in the oral composition in various amounts, such as an amount wherein the weight ratio of polyphosphate ion to anti-bacterial agent ranges from in excess of 0.72:1 to less than 4:1, or wherein the weight ratio of the anti-bacterial enhancing agent to the polyphosphate ion ranges from 1:6 to 2.7:1, or wherein the weight ratio of the anti-bacterial enhancing agent to the polyphosphate ranges from 1:6 to 2.7:1. Other useful anti-calculus agents include polycarboxylate polymers and polyvinyl methyl ether/maleic anhydride (PVM/MA) copolymers, such as GANTREZ®.

Particularly preferably, the oral care composition includes a halogenated diphenyl ether and a PVM/MA copolymer.

The composition may comprise one or more chelating agents able to complex calcium found in the cell walls of the bacteria. Binding of this calcium weakens the bacterial cell wall, augments bacterial lysis, and reduces the formation of plaque. These anti-calculus agents may for example comprise a polyphosphate, e.g., pyrophosphate, tripolyphosphate, or hexametaphosphate, e.g., in sodium or potassium salt form. One group of chelating agents which may be useful in the present invention are soluble pyrophosphate salts. Pyrophosphate salts include alkali metal pyrophosphate salts. Salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition at least 0.1%, e.g., from 0.5% to 5%, 1% to 3%, or 2% by weight of the composition.

Oral care compositions may include one or more enzymes. Useful enzymes include any of the available proteases, glucanohydrolases, endoglycosidases, amylases, mutanases, lipases and mucinases or compatible mixtures thereof. The enzyme may be a protease, dextranase, endoglycosidase or mutanase. The enzyme may be papain, endoglycosidase or a mixture of dextranase and mutanase. Enzymes may for example be present in an amount of 0.002% to 2.0% by weight of the composition, or 0.05% to 1.5% by weight of the composition, or 0.1% to 0.5% by weight of the composition.

Oral care compositions may comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g. monosodium citrate, disodium citrate, monosodium malate, etc.), alkali metal hydroxides such as sodium hydroxide, carbonates such as sodium carbonate, bicarbonates, sesqui carbonates, borates, silicates, phosphates (e.g. monosodium phosphate, trisodium phosphate, pyrophosphate salts, etc.), imidazole and the like. One or more pH modifying agents are optionally present in a total amount effective to maintain the composition in an orally acceptable pH range.

An oral care composition may comprise at least one colorant. Colorants herein include pigments, dyes, lakes and agents imparting a particular luster or reflectivity such as pearling agents. Any orally acceptable colorant may be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxy chloride, and the like. One or more colorants are optionally present in a total amount of from 0.001% to 20%, for example, from 0.01% to 10%, or from 0.1% to 5% by weight of the composition.

The oral care composition may comprise a herbal extract. Examples of herbal extracts are provided in U.S. Pat. No. 6,500,409, WO2011068815, U.S. Pat. No. 6,264,926, U.S. Pat. No. 7,083,779, US2009/0087501, and US2007/0116652.

Typically, a toothpaste may comprise at least an abrasive, an anti-caries agent, and a humectant.

Particularly preferred oral care compositions include those described in US2007/0140990 and US 2013/0266521.

Specific examples of toothpaste compositions are set out in the Examples (see Tables 2, 3 and 4). Variants of these compositions, in which the amounts of the ingredients may vary by ±25%, ±10%, or ±5%, are contemplated herein.

Benzyl alcohol may act as an antimicrobial agent. Accordingly, the compositions described herein are preferably substantially free of further preservatives, or are substantially free of parabens. A composition is substantially free of further preservatives if no further preservatives are present, or if only trace amounts of further preservatives are present. Trace amounts are amounts which would not produce a measurable preservative effect. Compositions comprising less than 100 ppm, less than 50 ppm, less than 10 ppm, or most preferably less than 1 ppm of further preservatives by weight may be considered substantially free of further preservatives.

The amount of benzyl alcohol is also not particularly limited, and may be selected as desired to provide a defoaming effect. In general, the higher the concentration of benzyl alcohol present, the stronger the defoaming effect. The amount of benzyl alcohol present in the composition will usually not exceed 5% by weight of the composition.

For certain applications, it is desirable for the composition to be capable of foaming, even when such foaming is undesirable during manufacture of the composition. This is particularly the case for toothpastes, which are required in some territories to have a minimum foaming power. As used herein, "foaming power" means the volume of foam in mL produced when a 5 g sample of the composition is tested using the method described by Hossain et al (IJPI's Journal of Pharmaceutics and Cosmetology, 2013, vol 3, issue 13, pp 24-28). This method is outlined in Example 3.

The Bureau of Indian Standards requires toothpastes to have a minimum foaming power of 50 mL. Accordingly, it is preferable to select the amount of benzyl alcohol such that the foaming power of the composition is at least 50 mL. The amount may vary depending on the nature and the amount of the surfactant present in the composition.

For example, benzyl alcohol may be included in the composition in an amount in the range 0.1% to 0.7% by weight of the composition. Preferably, the benzyl alcohol is included in the composition in an amount in the range 0.25% to 0.35% by weight of the composition. These amounts were found to result in a toothpaste which had a foaming power of at least 50 mL and to be effective in defoaming the toothpaste during manufacture when using a sodium lauryl sulfate (SLS) surfactant in amounts in the range 1.5% to 3% by weight of the composition.

It has surprisingly been found that a stronger defoaming effect is observed when benzyl alcohol is used in combination with a foam-reducing flavour. The combined use of benzyl alcohol and a foam-reducing flavour therefore provides an improved defoaming effect in comparison to the use of either component alone.

A foam-reducing flavour is a flavour which reduces the surface energy of air bubbles in water. Useful foam-reducing flavours include oils and alcohols. Oils may form a thin layer having a lower surface tension than water. Alcohols may reduce the surface tension and density of water. The foam-reducing flavour may comprise one or more essential oils, e.g. oils extracted from a plant by distillation. The foam-reducing flavour may be selected from: vanillin; sage; marjoram; parsley oil; spearmint oil; cinnamon oil; oil of wintergreen (methyl salicylate); peppermint oil; clove oil; bay oil; anise oil; *eucalyptus* oil; citrus oils; fruit oils and essences including those derived from lemon, orange, lime, grapefruit, apricot, banana, grape, apple, strawberry, cherry, pineapple; etc. bean- and nut-derived flavours such as coffee, cocoa, cola, peanut, almond, etc.; and menthol, menthyl acetate, menthyl lactate, camphor, *eucalyptus* oil, eucalyptol, anethole, eugenol, *cassia*, oxanone, a-irisone, propenyl guaiethol, thymol, linalool, benzaldehyde, cinnamaldehyde, N,2,3-trimethyl-2-isopropylbutanamide, 3-(1-menthoxy)-propane-1,2-diol, cinnamaldehyde glycerol acetal (CGA), and menthone glycerol acetal (MGA). Preferred foam-reducing flavours include those having 8 to 12 carbon atoms, at least one terminal dimethyl group, and a non-terminal OH group. The use of a foam reducing flavour is preferred, but also contemplated herein is the use of other oils or alcohols.

The foam-reducing flavour may be an essential oil. Preferred foam-reducing flavours include those having 8 to 12 carbon atoms, at least one terminal dimethyl group, and a non-terminal OH group.

The amount of foam-reducing flavour is not particularly limited, and may be selected as desired. For example, the foam-reducing flavour may be included in the oral care composition in an amount in the range 0.1% to 5% by weight of the composition. The foam-reducing flavour may preferably be used in an amount in the range 0.5% to 1.5% by weight of the composition. An alternative preferred range is 4.5% to 5% by weight of the composition.

Examples of methods of manufacturing oral care compositions which make use of benzyl alcohol to defoam a composition comprising at least one surfactant will now be described. It will be appreciated that any of the features discussed in relation to the use aspect of the present invention, in particular the ingredients and amounts used, are applicable to the following methods.

In the following methods, benzyl alcohol serves to accelerate the breakdown of foam and/or to reduce the volume of foam generated. Although methods of manufacturing oral care compositions comprising benzyl alcohol have been disclosed previously, e.g. in US2013/0064779, the defoaming properties of benzyl alcohol were not identified or exploited.

In one arrangement, a method of manufacturing an oral care composition may comprise:
(a) forming an oral care base composition;
(b) subsequently combining the oral care base composition with a defoaming agent and a surfactant to form the oral care composition; and
(c) defoaming the oral care composition,
wherein the defoaming agent is benzyl alcohol and wherein the defoaming agent is combined with the oral care based composition no later than the surfactant.

By adding the defoaming agent to the oral care composition no later than the surfactant, the generation of foam is inhibited. Preventing or reducing the formation of foam in this manner means that a batch of a given mass occupies a smaller volume. Larger batches may therefore be produced in a given reaction vessel. This improves the efficiency of the manufacturing process. The length of time taken to defoam the composition is also reduced, further improving efficiency. Reducing the time taken to defoam the composition may reduce energy usage, because the length of time for which the batch is stirred may be reduced. If present, foams may not mix efficiently with a liquid phase, which may lead to inconsistencies in the finished product. Preventing the formation of foam therefore also makes the process more reliable.

The method includes forming an oral care base composition. An oral care base composition is an intermediate product which is a mixture of two or more oral care ingredients. Examples of oral care ingredients include orally-acceptable solvents and carriers, e.g water; abrasives, e.g. abrasive silicas and calcium carbonate; anti-caries agents, e.g. fluoride sources and arginine sources; anti-calculus agents; vitamins; polymers; enzymes; humectants; thickeners; antimicrobial agents; preservatives; whitening agents; colorings and combinations thereof. An oral care base composition may have any pH; the oral care base composition may be acidic, neutral or alkaline but is preferably neutral or alkaline. Usually, an oral care base composition will not comprise a foam-reducing flavour or a surfactant.

Oral care ingredients may optionally be mixed at a temperature in the range of 30 to 70° C., or 40 to 60° C. in order to form the oral care base composition. Mixing may be carried out under vacuum, e.g. at a pressure in the range of 66 kPa to 93 kPa (about 500 to 700 mm Hg).

The present method will generally be carried out under continuous stirring. The stir speed may be varied as appropriate throughout the process or may be constant.

Step (a) of the method may comprise:
(i) forming a gel comprising a humectant; and
(ii) combining the gel with one or more further components to form the oral care base composition;

wherein the further components comprise one or more of a thickener and an abrasive.

In step (b) of the method, the defoaming agent is added to the oral care base composition not later than the surfactant. The defoaming agent may be added before the surfactant. The defoaming agent and the surfactant may be added substantially simultaneously.

As used herein, "substantially simultaneously" means that the defoaming agent is added to the oral care base composition before foam is formed. In the absence of a defoaming agent, foam would generally begin to form rapidly after the addition of the surfactant. The defoaming agent may be added up to 1 minute after the addition of the surfactant, up to 30 seconds after the addition of the surfactant, up to 10 seconds after the addition of the surfactant, or preferably no more than 1 second after the addition of the surfactant. Adding the defoaming agent at the same time as the surfactant has been found to produce the strongest defoaming effect.

The simultaneous addition of the surfactant and the benzyl alcohol may be achieved by forming a pre-mix comprising the benzyl alcohol and the surfactant.

As indicated above, the combined use of benzyl alcohol and a foam-reducing flavour to defoam a composition is provided herein. When a pre-mix is used in the present method, the pre-mix preferably comprises the benzyl alcohol, the at least one surfactant, and the foam-reducing flavour. A further lipophilic ingredient may be included in the pre-mix. In this way, the pre-mix may be used to mix the lipophilic ingredient with the oral care base composition, thereby improving the uniformity of the oral care composition and/or reducing the amount of stirring required in comparison to a process in which the lipophilic ingredient is added directly to the oral care base composition.

Various methods may be used to defoam the composition in step (c). For example, step (c) may comprise stirring the oral care composition under vacuum, for example at a pressure of 66 kPa to 93 kPa (500 mm Hg to 700 mm Hg), and preferably a pressure of 80 kPa to 93 kPa (about 600 mm Hg to about 700 mm Hg). Alternatively, step (c) may comprise allowing the composition to settle at room temperature and pressure. Step (c) may have a duration of 12 minutes or less, preferably 10 minutes or less, more preferably 8 minutes or less, or even more preferably 5 minutes or less.

In another arrangement, a method of using benzyl alcohol as a defoaming agent in the manufacture of an oral care composition comprises the steps of:
  (i) mixing benzyl alcohol and a surfactant with an oral care base composition; and
  (ii) stirring the resulting mixture under vacuum to defoam the mixture;
wherein the vacuum is applied no later than 4 minutes after step (i).

This method makes use of the surprising ability of benzyl alcohol to act as a defoaming agent. In this method, the benzyl alcohol and the surfactant are mixed with the oral care base composition at about the same time. This reduces the formation of foam. In this method, the benzyl alcohol may be added to the oral care base composition shortly before the surfactant, shortly after the surfactant, or substantially simultaneously to the surfactant. The strongest defoaming effect is observed when the surfactant and the benzyl alcohol are mixed with the oral care base composition substantially simultaneously.

A pre-mix may be formed before step (i). The pre-mix may comprise two or more ingredients selected from the benzyl alcohol, the at least one surfactant, and a foam-reducing flavour.

In a conventional process, vacuum is not applied until 5 minutes or more have passed after the addition of the surfactant. This is because large amounts of foam would be generated if the vacuum is applied before the surfactant is distributed throughout the composition. It has been found that when benzyl alcohol is used as a defoaming step, it is not necessary to stir the composition for an extended period of time between adding the surfactant and applying the vacuum. The use of benzyl alcohol therefore allows for the faster manufacture of the oral care composition.

Accordingly, when using benzyl alcohol, the time between adding the surfactant and applying the vacuum is 4 minutes or less. The time between step (i) and applying the vacuum is preferably minimized. For example, the time between step (i) may be 3 minutes or less, 2 minutes or less, 1 minute or less, or particularly preferably 30 seconds or less. Vacuum may be applied before the addition of the benzyl alcohol and the surfactant such that the oral care base composition is under vacuum when the benzyl alcohol and the surfactant are added.

Step (ii) comprises stirring the mixture under vacuum to defoam the mixture. The mixture is stirred under a pressure which is lower than atmospheric pressure. For example at the pressure may be in the range of 66 kPa to 93 kPa (500 mm Hg to 700 mm Hg), and is preferably in the range of 80 kPa to 93 kPa (about 600 mm Hg to about 700 mm Hg).

As noted above, the ingredients of the oral care composition produced by this method, their amounts, and their functions may be as described with reference to the use aspect of the present invention.

EXAMPLES

The present invention will now be explained by reference to the following non-limiting Examples.

Example 1: Defoaming Properties of Benzyl Alcohol

The defoaming properties of benzyl alcohol were compared to those of a positive control and a negative control. Benzyl alcohol was found to have useful defoaming properties.

Three aqueous solutions of 0.2% sodium lauryl sulfate were prepared in 250 mL measuring cylinders by diluting 5 g of a 2% sodium lauryl sulfate stock solution with water to give a total volume of 50 mL. The solutions were agitated by swirling the measuring cylinders 12 times to generate foam. The volumes of foam generated were recorded. A 1 mL aliquot of defoaming agent was then added to each of the solutions at a rate of 0.01 mL/s. The defoaming agents investigated were benzyl alcohol, methanol, and water. Three minutes after the addition of the defoaming agent, the volumes of foam present in each vessel were recorded. The results of this investigation are shown in Table 1.

TABLE 1 defoaming properties of benzyl alcohol compared to a positive control (methanol) and a negative control (water)

| Agent | Initial foam height | Final foam height | % reduction in foam after addition of defoaming agent |
|---|---|---|---|
| Water | 210 | 200 | 4.8 |
| Methanol | 220 | 56 | 74.5 |
| Benzyl Alcohol | 220 | 90 | 59.1 |

The data demonstrate that, as expected, water does not produce a significant defoaming effect. Both methanol and benzyl alcohol were effective in reducing the volume of foam. Benzyl alcohol produced a 59.1% reduction in the volume of foam, with methanol producing a somewhat larger reduction (74.5%). Despite its excellent defoaming properties, methanol is known to be toxic and is therefore unsuitable for inclusion in oral care compositions. In contrast, benzyl alcohol may be safely included in oral care compositions and provides additional useful functionality because it is an antimicrobial agent.

Example 2: Defoaming Properties of Benzyl Alcohol in an Oral Care Composition In order to illustrate further the defoaming properties of benzyl alcohol, the time taken to defoam a composition containing benzyl alcohol was compared to that for a comparative composition. Benzyl alcohol was found to reduce by 50% the time taken to defoam the composition.

The formulations of the compositions investigated are set out in Table 2.

TABLE 2 formulations for oral care compositions.

| Ingredient | Amount present in composition A (comparative)/% | Amount present composition B/% |
|---|---|---|
| Sorbitol 70% | 40 | 40 |
| GANTREZ S-97 (B.F.) copolymer of methyl vinyl ether and maleic acid | 2 | 2 |
| PS-223 carrageenan concentrate | 0.85 | 0.85 |
| Sodium saccharin | 0.3 | 0.3 |
| Sodium fluoride | 0.22 | 0.22 |
| Sodium hydroxide solution 50% | 1.2 | 1.2 |
| ZEODENT-114 abrasive silica | 13 | 13 |
| ZEODENT-165/MFIL P thickener silica | 5 | 5 |
| Foam-reducing flavour | 1.0 | 1.0 |
| Triclosan | 0.3 | 0.3 |
| Sodium Lauryl Sulfate Granules | 2 | 2 |
| Purified Water | Q.S | Q.S |
| Titanium Dioxide | 0.5 | 0.5 |
| Benzyl Alcohol | — | 0.3 |
| Total | 100 | 100 |

The compositions were manufactured as follows:
1. The sorbitol was added to an SS vessel having a stirrer. The stirrer was started. The sorbitol was heated to 60-62° C.
2. Half of the purified water was added to the SS vessel.
3. The copolymer of methyl vinyl ether and maleic acid was added to the SS vessel and mixed. Mixing was continued until the copolymer of methyl vinyl ether and maleic acid was fully dispersed.
4. The NaOH (50% solution) was added to the SS vessel and mixed for 5 minutes.
5. The remaining purified water was added to the SS vessel.
6. A pre-mix of the PS-223, the sodium saccharin and the sodium fluoride was formed. The pre-mix was added to the SS vessel.
7. The resulting gel was mixed for 20 minutes at a temperature of 64-67° C.
8. The gel was transferred to a mixer. The thickener silica was added to the mixer and mixed for 5 minutes. The mixer used in the present experiment was an Alpro mixer.
9. The abrasive silica and titanium dioxide were added to the mixer and mixed under vacuum. Mixing was continued until the temperature reached 46° C.
10. At 46° C., the flavor, triclosan and sodium lauryl sulfate granules were added to the mixture. If used, benzyl alcohol was also added at this stage.
11. The resulting mixture was then stirred for 2 minutes. Vacuum was then applied. The time taken for the batch to settle was observed.
12. After allowing the batch to settle, mixing was continued for a further 8 minutes. The vacuum was then released, and the oral care composition collected.

The batches of the comparative composition and of the example composition were each 4 kg in size.

The time taken to defoam the composition A was 60 seconds. The time taken to defoam composition B was 30 seconds. Thus, the inclusion of benzyl alcohol in the oral care composition reduced the defoaming time by about 50%. The use of benzyl alcohol therefore allows the time taken to produce a batch of oral care composition to be reduced.

Generally, the time taken to defoam a given composition increases with the batch size. It is predicted that larger reductions in defoaming time would be observed for larger batches. The present inventors have found that if a defoaming step takes about 1 minute in a laboratory scale process (batch size of the order 4 kg), then the corresponding step in a large scale process (batch size of the order 3000 kg) might be expected to take 5 to 10 minutes.

Example 3: Foaming Properties of the Oral Care Compositions of Example 2

The Bureau of Indian Standards requires toothpaste compositions to have a foaming power of not less than 50 mL. The foaming power of the oral care compositions produced in Example 2 was therefore investigated.

Foaming power was measured using the method described by Hossain et al (IJPI's Journal of Pharmaceutics and Cosmetology, 2013, vol 3, issue 13, pp 24-28). Briefly, a 5 g sample of each composition was allowed to stand in 10 mL of water for 30 minutes. The mixture was stirred and transferred to a 250 mL measuring cylinder. The volume present in the cylinder was adjusted to 250 mL with water. The resulting suspension was stirred and heated to 30° C. The cylinder was stoppered and inverted 12 times to generate foam, and allowed to stand for 5 minutes. The volume of foam generated was then recorded. The volume of foam generated is equivalent to the foaming power.

Composition A had a foaming power of 180 mL. Composition B had a foaming power of 120 mL.

The data demonstrate that the inclusion of benzyl alcohol in an oral care composition reduces the overall foaming power of the composition. However, the foaming power is maintained well above the minimum required by the Bureau of Indian Standards. Therefore, a reduction in the time taken to produce the composition is achieved without impacting negatively on the properties of the finished composition.

Example 4: Microbiological Robustness and Foaming Power of Silica-Based Oral Care Compositions Further oral care compositions were prepared in accordance with Table 3. These compositions included a silica abrasive. The microbiological robustness, a measure of the resistance to microbial spoilage, and foaming power of the compositions were investigated.

TABLE 3 oral care compositions comprising silica abrasives

| Ingredients | Amount present in composition C (comparative)/ % (w/w) | Amount present in composition D % (w/w) |
| --- | --- | --- |
| Sorbitol 70% | 40 | 40 |
| GANTREZ S-97 (B.F.) copolymer of methyl vinyl ether and maleic acid | 2 | 2 |
| PS-223 carrageenan concentrate | 1 | 0.85 |
| Sodium saccharin | 0.3 | 0.3 |
| Sodium fluoride | 0.221 | 0.221 |
| Sodium hydroxide solution, 50% | 1.375 | 1.2 |
| ZEODENT-114 abrasive silica | 20 | 13 |
| ZEODENT-165/MFIL P thickener silica | 1.5 | 5 |
| Foam-reducing flavour | 1.0 | 1.0 |
| Triclosan | 0.3 | 0.3 |
| SLS granules | 2 | 2 |
| water | q.s. | q.s. |
| Minors | 0.7 | 0.7 |
| Benzyl Alcohol | — | 0.3 |

The minors included in the above compositions were pigments. These components are not believed to influence significantly the foaming properties of the compositions.

The foaming power of compositions C and D was determined using the method of Hossain et al as described in Example 3. Composition C had a foaming power of 106 mL, and composition D had a foaming power of 50 mL. The foaming power of composition D remained within the specification laid down by the Bureau of Indian Standards. Since the foaming power of composition D was lower, this composition would be expected to defoam more quickly during manufacturing.

Microbiological robustness testing (MRT) was used to assess the ability of the compositions to withstand microbial insult. The method involves inoculating a test material with a standard bacterial inoculum. The inoculum includes at least 11 strains of bacteria. The test material is then sampled at defined intervals. The surviving bacteria at each time interval are recovered by dilutions and platings. The log reductions in the number of bacteria are plotted, and the microbiological robustness index is determined from the area under the curve. The higher the microbiological robustness index, the greater the resistance to microbial insult. Microbiological robustness indices greater than or equal to 0.75 are considered good.

Composition C was found to have a microbiological robustness index of 0.63. Composition D had a microbiological robustness index of 1.0.

The data demonstrate that benzyl alcohol is effective as an antibacterial agent as well as a defoaming agent. Obtaining two different functions from the same material is useful because it may allow for the simplification of the oral care formulation, allowing easier production and potentially a reduction in manufacturing costs.

Example 5: Microbiological Robustness and Foaming Power of Calcium Carbonate-Based Oral Care Compositions To illustrate that benzyl alcohol has useful functionality in a broad variety of oral care compositions, compositions comprising a precipitated calcium carbonate abrasive were prepared and characterized. The formulations of these compositions are set out in Table 4.

TABLE 4 calcium carbonate based oral care compositions

| Ingredients | Amount present in composition E (comparative)/ % w/w | Amount present in composition F/ % w/w | Amount present in composition G/ % w/w |
| --- | --- | --- | --- |
| Sorbitol | 35 | 35 | — |
| Glycerin | — | — | 24.5 |
| PS223 caragenan concentrate | 0.825 | 0.825 | 0.825 |
| Sodium Saccharin | 0.27 | 0.27 | 0.27 |
| Sodium Silicate | 1 | 1 | 1 |
| Purified Water | q.s. | q.s. | q.s. |
| Sodium Bicarbonate | 0.5 | 0.5 | 0.5 |
| Sodium monofluorophosphate | 0.76 | 0.76 | 0.76 |
| Thickener silica | 1.75 | 1.75 | 1.75 |
| Precipitated calcium carbonate | 39 | 39 | 39 |
| Triclosan | 0.27 | 0.27 | 0.25 |
| SLS Granules | 2.5 | 2.5 | 2.5 |
| Benzyl Alcohol | — | 0.3 | 0.3 |
| Flavor | 0.95 | 0.95 | 0.95 |
| Titanium dioxide | 1 | 1 | — |

The foaming power and microbiological robustness of each of these compositions were determined using the methods outlined in Examples 3 and 4. Results of these analyses are set out in Table 5, below.

TABLE 5 analyses of oral care compositions

| Composition | Foaming power/mL | Microbiological robustness |
| --- | --- | --- |
| Composition E (comparative) | 200 | 0.59 |
| Composition F | 170 | 1 |
| Composition G | 170 | 1 |

The data shown in the Table illustrate that the compositions comprising benzyl alcohol have reduced foaming power and increased microbiological robustness. Benzyl alcohol is therefore useful as a defoaming agent and as an antimicrobial agent.

What is claimed is:

1. A method of manufacturing an oral care composition, which method comprises:
   a. forming an oral care base composition;
   b. subsequently combining the oral care base composition with a defoaming agent and at least one surfactant to form the oral care composition; and
   c. defoaming the oral care composition,
   wherein the defoaming agent is benzyl alcohol; and
   wherein the defoaming agent is combined with the oral care base composition no later than the at least one surfactant,
   and wherein step (c) comprises stirring the oral care composition under vacuum at a pressure in the range of 66 kPa to 93 kPa.

2. The method of claim 1, wherein the oral care composition comprises a foam-reducing flavour.

3. The method of claim 2, wherein the foam-reducing flavour is included in the oral care composition in an amount in the range 0.5% to 1.5% by weight of the oral care composition.

4. The method of claim 2, wherein step (b) comprises:
   (i) forming a pre-mix comprising the defoaming agent and the foam-reducing flavour; and
   (ii) combining the pre-mix with the oral care base composition.

5. The method of claim 4, wherein the pre-mix further comprises a halogenated diphenyl ether or a herbal extract.

6. The method of claim 5, wherein the pre-mix comprises a halogenated diphenyl ether which is triclosan.

7. The method of claim 4, wherein the pre-mix further comprises the at least one surfactant.

8. The method of claim 1, wherein the benzyl alcohol is included in the oral care composition in an amount in the range 0.1% to 0.7% by weight of the oral care composition.

9. The method of claim 8, wherein the benzyl alcohol is included in the oral care composition in an amount in the range 0.25% to 0.35% by weight of the oral care composition.

10. The method of claim 1, wherein the at least one surfactant comprises an anionic surfactant.

11. The method of claim 10, wherein the anionic surfactant comprises sodium lauryl sulfate or sodium lauroyl sarcosinate.

12. The method of claim 1, wherein the at least one surfactant comprises a betaine surfactant, a polysorbate surfactant, and/or a poloxamer surfactant.

13. The method of claim 1, wherein step (a) comprises:
   (i) forming a gel comprising a humectant; and
   (ii) combining the gel with one or more further components to form the oral care base composition;
   wherein the further components comprise one or more of a thickener and an abrasive.

14. The method of claim 1, wherein step (c) has a duration of 10 minutes or less.

15. The method of claim 1, wherein the oral care composition is substantially free of parabens.

16. The method of claim 1, wherein the oral care composition includes a copolymer of methyl vinyl ether and maleic anhydride.

* * * * *